(12) United States Patent
Raidt et al.

(10) Patent No.: US 10,285,791 B2
(45) Date of Patent: May 14, 2019

(54) INJECTION DEVICE FOR ADMINISTRATION OF AN INJECTION TO AN ANIMAL

(71) Applicant: Henke-Sass, Wolf GmbH, Tuttlingen (DE)

(72) Inventors: Simon Raidt, Wurmlingen (DE); Frank Altermann, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 131 days.

(21) Appl. No.: 15/380,422

(22) Filed: Dec. 15, 2016

(65) Prior Publication Data

US 2017/0172718 A1 Jun. 22, 2017

(30) Foreign Application Priority Data

Dec. 17, 2015 (DE) .................. 10 2015 122 069

(51) Int. Cl.
| | |
|---|---|
| *A61D 7/00* | (2006.01) |
| *A61M 5/172* | (2006.01) |
| *A61M 5/19* | (2006.01) |
| *A61D 1/02* | (2006.01) |
| *A61M 5/142* | (2006.01) |
| *A61M 5/20* | (2006.01) |
| *A61M 5/32* | (2006.01) |

(52) U.S. Cl.
CPC .............. *A61D 7/00* (2013.01); *A61D 1/025* (2013.01); *A61M 5/172* (2013.01); *A61M 5/19* (2013.01); *A61M 5/14248* (2013.01); *A61M 5/20* (2013.01); *A61M 5/204* (2013.01); *A61M 5/3298* (2013.01); *A61M 2005/14252* (2013.01); *A61M 2005/206* (2013.01); *A61M 2005/208* (2013.01); *A61M 2005/2026* (2013.01); *A61M 2205/332* (2013.01); *A61M 2205/587* (2013.01); *A61M 2250/00* (2013.01)

(58) Field of Classification Search
CPC ... A61D 7/00; A61M 5/172; A61M 2205/332; A61M 2250/00
See application file for complete search history.

(56) References Cited

U.S. PATENT DOCUMENTS

| | | | |
|---|---|---|---|
| 3,859,996 | A | 1/1975 | Mizzy et al. |
| 4,276,879 | A | 7/1981 | Yiournas |
| 5,681,291 | A | 10/1997 | Galli |
| 8,211,058 | B2 | 7/2012 | Jorna |
| 2010/0004624 | A1 | 1/2010 | Hunter |

(Continued)

*Primary Examiner* — Bradley J Osinski
(74) *Attorney, Agent, or Firm* — Skaar Ulbrich Macari, P.A.

(57) ABSTRACT

An injection device for administration of an injection to an animal can include a main body, which contains an injection instrument, a contact device, which has a contact area which is shaped in conformity with a body part of the animal to which the injection is to be administered. A support device which supports the contact device on the main body can be movable in a pressure application direction. A force measurement device including at least one force sensor can be designed to measure at last one force with which the contact device acts on the main body. A control device can activate the injection instrument if the force measured by the force measurement device lies in a specified range.

20 Claims, 6 Drawing Sheets

(56) References Cited

U.S. PATENT DOCUMENTS

2014/0330203 A1* 11/2014 McLoughlin .......... A61M 5/20
604/131
2016/0051352 A1* 2/2016 Moons ................... A61D 1/025
604/65

* cited by examiner

INJECTION DEVICE FOR ADMINISTRATION OF AN INJECTION TO AN ANIMAL

PRIORITY

This application claims the benefit of German Patent Application No. 102015122069.5, filed on Dec. 17, 2015, which is hereby incorporated herein by reference in its entirety.

FIELD

The present invention relates to an injection device for administration of an injection to an animal, which comprises a main body and a contact device. The main body comprises an injection instrument and the contact device has a contact area which is shaped in conformity with a body part of an animal to which the injection is to be administered.

BACKGROUND

In the keeping and rearing of animals, it is often necessary to administer an injection to the animals. This can be carried out manually with a conventional syringe. In larger enterprises, for example in poultry farming, many animals are present, to which an injection has to be administered in as short a time as possible. Hence in the prior art there are injection devices by means of which an injection to an animal can be carried out more rapidly.

For example, U.S. Pat. No. 8,211,058 B2 discloses a device for injection into the breast muscle of a chicken. For this, the device has a pressure application surface which is matched to the anatomy of the chicken in the region of the breast muscle. Through the shaping of the pressure application surface, correct positioning of the bird is facilitated. In addition, three contact sensors are provided in the pressure application surface, which are activated on correct positioning of the chicken on the pressure application surface. If all three contact sensors are activated by the presence of the chicken, a control device triggers the injection into the breast muscle of the chicken.

However, there is a continuing need to provide an improved injection device for administration of an injection to an animal.

SUMMARY

The disclosure includes an injection device for administration of an injection to an animal. The device can include a main body with an injection instrument, a contact device, a support device, a force measurement device and a control device. The contact device comprises a contact area which is shaped in conformity with a body part of the animal to which the injection is to be administered. The support device supports the contact device on the main body movable in a pressure application direction. The force measurement device has at least one force sensor and is designed to measure the force (preferably in the pressure application direction) with which the contact device acts on the main body. The control device activates the injection instrument if the force measured by the force measurement device lies in the specified range.

The injection device serves in particular for the administration of a great variety of active substances which have to be administered subcutaneously and/or intramuscularly. For example by means of the injection device vaccines or medicaments can be administered to the animal. In particular, by means of the injection device medicaments for the treatment of a great variety of diseases can be administered.

The injection device, in particular the contact device, can be designed for the injection of a great variety of animals. The contact device is differently shaped depending on the animal to be treated (and optionally on its age). In particular, the injection device is intended for administration of an injection to poultry, such as for example chickens, ducks, turkeys, quail, geese, pigeons or other farmed poultry.

The main body may comprise in particular a housing and a stand device by means of which the injection device can be put down on a support. A recess in the housing, which for example provides an access to the injection instrument, can be closed by a cover. Furthermore, the control device is preferably arranged on or in the main body. In addition, a power supply such as for example a transformer or a battery can be provided for the injection instrument, the control device and/or the force measurement device. The injection instrument is in particular positioned in the main body, especially within the housing of the main body.

The injection instrument can be configured as a syringe, such as for example a self-filling syringe. The syringe can have a syringe cylinder, in which a plunger is movably located, and a cannula whereby by movement of the plunger in the direction towards the cannula the fluid present in the syringe cylinder (i.e. for example the vaccine or the desired medicament) can be discharged via the cannula. The injection instrument further preferably comprises an actuator which can move the syringe in the direction of the contact device, so that the cannula can be inserted into the part of the animal which is adjacent to the contact area, for example through an opening in the contact area. After this insertion process, the medicament or the active substance can then be administered by movement of the plunger. In particular, the cannula can be inserted into the breast muscle of the bird.

The injection instrument can include one or more syringes. In particular, it can have two syringes so that two different medicaments can be administered simultaneously to an animal.

The injection instrument can be designed such that the several syringes can be moved in the direction of the contact device simultaneously or independently of one another.

The injection instrument can however additionally or alternatively have any other type of injection device with which the desired injection can be administered to the animal lying against the contact area.

By means of the actuator, an end of the injection device on the discharge side can be moved to the animal lying against the contact area. Contact with the animal may or also may not be achieved. It is in particular essential that the desired injection can be carried out reliably.

The injection device can be configured such that the injection devices (e.g. syringes) are controllable independently of one another. Thus for example for a first injection procedure only one of the injection devices may be used. For a second injection procedure, two or more devices may then be used. During each injection procedure the relevant fluids (e.g. medicaments) can each be administered to several animals. The injection device can have an input interface via which the desired injection procedure is adjustable and/or selectable.

The contact area of the contact device can be shaped like the body part of the animal to which the injection is to be administered. For example, the injection can be administered into the breast muscle of a bird, in which case the contact area is then shaped like the breast of the bird.

Alternatively, the contact device can be designed for injection into the neck or the foot of a bird. Then the contact area has a shape adapted thereto.

In particular, several contact devices can be assigned to the injection device, so that by means of one injection device injections can be administered to several different animal species or at different sites. For this, the contact device is in particular designed such that it can be detachably secured to the main body. The contact area of the contact devices is for example designed appropriately adapted with regard to the animal species, the animal breed, the age of the animal and/or the size of the animal.

The support device preferably makes it possible to secure the contact device to the main body, in particular detachably. The support device makes it possible for the contact device to be arranged movable on the main body, so that the contact device, preferably for the determination of the pressing force, can be moved towards the main body in a pressure application direction. This pressure application is in particular carried out in that the animal is pressed against the contact device and thereby the contact device is moved towards the main body.

The force measurement device can be provided to measure the force which the contact device exerts on the main body. In particular, the force measurement device serves to determine the pressing force of the animal against the contact device. The force measurement device is in particular provided on the main body. The contact device can thus be designed free from electrical components, since the force measurement device and also the control device is arranged on the main body. The contact device is thus in particular a pure molded component. The contact device can be produced by injection molding or deep-drawing.

The control device can for example be realized by means of a microprocessor or an electrical switching circuit. The control device activates the injection instrument, which for example takes place through the triggering of the actuator of the injection instrument, so that after the activation of the injection instrument, the needle is moved outwards from the main body and the injection preparation is conveyed through the needle.

The activation of the injection instrument can then take place when the measured force lies in a specified range. This means in particular that an injection is carried out if the pressing force of the animal against the contact device lies in a specified range. The specified range can for example comprise those forces which are greater than a specified threshold value. Alternatively the specified range can represent a lower and upper limit for the pressing force of the animal against the contact device. The specified range can thus be a range open at one end and also a range bounded at both ends.

The invention in certain embodiments has the advantage that all electrical components are preferably arranged on the main body, so that the contact device is free from electrical devices. Thus the production of the contact device is possible particularly economically, since only the contact area has to be shaped in conformity with the body parts of the animal, without in comparison to the prior art further pressure sensors and their wiring having to be provided on the contact device. In addition, in the injection device according to the present invention it is not necessary to make an electrical connection between the main body and the contact device, since in particular all electrical components are arranged on the main body. This also simplifies the production of the injection instrument.

A further advantage of certain embodiments is that the force measurement device makes it possible for a user of the injection device to simplify the injection. For only when the pressing force of the animal lies in the specified range is the injection administered. Since the pressing force is a measure of the fact that the animal has been correctly positioned in the contact area of the contact device, the injection takes place at the correct site. Thus with appropriate choice of the specified range, too light a pressing, which as a rule corresponds to unsatisfactory pressing of the animal on to the contact area, and/or too firm a pressing, which can result in deformations of the animal by the pressing and hence an unplaced injection, can be avoided.

The force measurement device can comprise a first force sensor and a second force sensor at a distance therefrom, wherein the control device can only activate the injection instrument if the difference between the force measured by the first force sensor and the second force sensor lies below a specified value. In particular, both force sensors can be positioned at a distance in a horizontal direction from a midline of the contact area. In particular, the support device comprises three support elements, wherein the first support element comprises the first force sensor and/or the second support element comprises the second force sensor.

The support elements can be configured as projections on which the contact device, with in particular correspondingly shaped recesses, can move in the pressure application direction. For example, the support elements are designed as rods, pillars or cylinders, while the contact device has a corresponding, in particular cylindrical, cavity, so that the contact device can be moved towards the main body in the pressure application direction. In particular, the axial orientation of the cavity and of the support elements corresponds to the pressure application direction. Alternatively, one or more support elements can lie against a contact surface of the contact device, wherein the contact surface is preferably bounded in the circumferential direction at least in certain areas by a side wall. The side walls serves in particular for the positioning of the contact device on the main body.

The first force sensor and the second force sensor, which can measure the pressing force, can be incorporated in a first support element and a second element respectively. Preferably the first support element and the second support element, and thus also the first force sensor and the second force sensor, are arranged in a horizontal direction on the main body, so that it is possible with the first and the second force sensor to determine a force difference in a horizontal direction. The horizontal direction is in particular perpendicular to the orientation of the animal in the contact area. For example, the first support element and the second support element are arranged left and right of a vertical midline. The midline can represent the axis of symmetry of the contact area, wherein the first force sensor and the second force sensor are arranged symmetrically to this midline. With the force sensors it is thus possible to determine a balance of the pressing force in the horizontal direction. Horizontal and vertical relate for example to the base on which the main body stands and thus also to a floor area of the stand device.

The first and/or the second force sensor can be configured to measure a force acting thereon. The force sensor can be designed as a spring force transducer or as a piezo force transducer. In particular, the first and/or the second force sensor are designed as weighing cells, as is known from the prior art. The first and the second force sensor are preferably identically designed. Depending on the type of the force sensor, the required movability of the contact device relative to the main body in the pressure application direction varies. With use of a weighing cell, the contact device only has to be moved slightly in the pressure application direction.

The force sensor can be disposed on an end of the respective support element facing the contact device. Depending on the design of the force sensor, the contact device is moved in the direction of the main body, and thus the force sensor compressed, by the pressing force. Alternatively, by pressing of the contact device onto the main body the force sensor changes in its extension only slightly, wherein the pressing force is detected at the same time.

The control device preferably only activates the injection instrument if the difference between the force measured by the first force sensor and the second force sensor lies below a specified value. For example, the control device does not activate the injection instrument until the total force of the pressing of the animal against the contact device exceeds a certain threshold value and/or at the same time the difference between the force measured by the first and the second force sensor lies below a certain limit value. It is thus ensured that the total pressing force lies above a threshold value, so that it can be assumed that the animal is lying correctly in the contact area, wherein a different pressing onto one side of the contact area is at the same time avoided. This represents a further indication that the animal has been correctly positioned on the contact device, so that the injection is administered at the intended site. Thus an advantage of the provision of two force sensors claimed is that it can be better determined that the animal is lying correctly against the contact device, in particular as regards the balance of force in the horizontal direction.

The injection device can comprise a capacitive sensor for detecting the presence of the animal at the contact area, wherein preferably the control device can only activate the injection instrument if the capacitive sensor detects the presence of the animal. In particular a third support element of the support device comprises the capacitive sensor.

The capacitive sensor can operate on the basis of the change in the capacity of a single condenser or a whole condenser system. For example, the capacitive sensor is such as is known from the prior art. In a preferred embodiment the capacitive sensor is provided at an end of the third support element facing the contact device, so that it is designed to detect the proximity or presence of an animal. In particular, the contact device in the vicinity of the third support element is designed such that the measurement of the capacitive sensor is not affected. This can for example be carried out by appropriate choice of the material of the contact area in the region of the third support element.

The capacitive sensor, in particular the third support element, is preferably positioned such that it is in the vicinity of an upper region of the contact area. In particular, the capacitive sensor is positioned such that with its aid it can be determined whether the animal is present in a peripheral region, in particular the upper peripheral region of the contact area. For example, the third support element is arranged displaced in a vertical direction relative to the first and/or second support element. Preferably the third support element and/or the capacitive sensor are positioned on the midline of the contact device.

Through the preferred arrangement of the capacitive sensor such that it corresponds to a peripheral region of the contact area, it can with its aid be determined whether the animal is correctly lying against a peripheral region of the contact area. In particular, the control device activates the injection instrument if the capacitive sensor detects the presence of the animal, the total force lies above a specified threshold value and/or the measured force difference between the first force sensor and the second force sensor lies below a certain limit value. The result of this is that the correct positioning on the contact device can be especially well determined, which results in an injection at the desired site.

The contact area can comprise a contact section and a pressure application area which is movable towards the contact section in the pressure application direction. The pressure application area can for example have a movement range in the direction of the pressure application direction of at most 1 mm, 2 mm, 3 mm, 4 mm, 5 mm or at most 10 mm.

The pressure application area corresponds in particular to a part of the animal for which it is especially important that it is lying against the contact device. For example, the pressure application area serves for the contact of the breastbone and a part of the breast muscle of a bird or poultry. The correct positioning of the breastbone is an important indication that the injection can be carried out at the correct site of the breast muscle.

The contact section and the pressure application area together form the contact area, so that the contact section is also shaped in conformity with the anatomy of the animal to be pressed on. In particular, the contact section surrounds the pressure application area. The contact section in particular together with the pressure application area forms an essentially continuous contact surface for the animal to be treated (apart from a small gap between the outer contact section and the inner pressure application area).

The relative movability of the pressure application area relative to the contact section makes it possible to determine the correct positioning of the animal at the pressure application area separately from the positioning of the animal at the contact section. In particular, the movability of the pressure application area relative to the contact section provides a further parameter by means of which the positioning of the animal against the contact device can be determined.

The movability of the pressure application area relative to the contact section is preferably free from initial tension. For example, the pressure application area is mounted with play at the contact section. The pressure application area is in particular moved from the contact section towards the main body by the pushing of the animal against the contact device.

The contact section and/or the pressure application area can be produced from plastic or metal. In particular, these are produced by injection molding, wherein other production methods, such as for example deep-drawing, are also possible.

The pressure application area can sit in a recess of the contact section.

The contact section can surround the recess completely, so that the pressure application area can be supported only on the contact section. In this way, it is possible to produce a relative movement of the pressure application area with respect to the contact section.

The pressure application area can be attached to the contact section by means of a snap connection. This is preferably designed such that the snap connection cannot be non-destructively separated. Alternatively, the snap connection can be non-destructively released. The snap connection can be produced as known from the prior art. The snap connection enables the movability of the pressure application area relative to the contact section in the pressure application direction. Preferably, snap connections are provided at three sites along the recess.

The pressure application area can include at least one projection or one slot, wherein the contact section comprises at least the other of the projection and the slot, wherein the projection and the slot are provided with play in the pressure application direction.

The pair of projection and slot represents an example of a snap connection. Preferably, three pairs of projections and slots are provided. The slot can be designed as a recess into which the projection engages. For example, the pressure application area has three projections which engage with play in the slots of the contact section. The play is provided in particular in the pressure application direction, so that the pressure application area can move freely in the pressure application direction relative to the contact section.

The pair of projection and slot can also be designed circumferential around the pressure application area. The provision of a movable connection by means of projection and slot has the advantage that for attachment the pressure application area can be clicked into the contact section.

The force measurement device can include a third force sensor arranged on the main body, wherein the third force sensor is preferably designed to measure the force acting on the pressure application area. In this case, the first and second force sensor can measure the forces of the contact section.

The third force sensor can be provided separately from the support elements of the support device. In a preferred embodiment, the third force sensor does not contribute to the support of the contact device on the main body. Rather it serves for the measurement of a force which acts on the pressure application area. Thus with the aid of the third force sensor in conjunction with the movable arrangement of the pressure application area on the contact area it is possible additionally to check whether the animal is correctly positioned at the pressure application area.

The third force sensor can be a force sensor similar to the first and/or second force sensor. The third force sensor is preferably arranged opposite the pressure application area.

The control device can be configured to only activate the injection instrument if the force measured by the third force sensor lies in a specified range. Preferably, the specified range is a force range bounded at both ends. It can therefore be established by means of the third force sensor that the force acting on the pressure application area is not too great and not too small, which indicates the correct positioning of the animal against the pressure application area.

The control device can be configured to only activate the injection instrument when the force measured by the first and the second force sensor lies above a certain threshold value, the difference between the force measured by the first force sensor and the second force sensor lies below a certain limit value, the capacitive sensor detects the presence of an animal and/or the force measured by the third force sensor lies within the specified force range. This criterion is particularly well suited to indicating the correct positioning of the animal against the contact device. In particular, the positioning of the animal against the contact device takes place in that firstly the force balance in the horizontal direction is determined by means of the first and second force sensor. Then the pressing force is increased so that the animal lies against the pressure application area with appropriate force.

The control device can also be configured to activate the injection instrument if one of the aforesaid conditions or any combination of these conditions is fulfilled.

If the force measurement does not fulfil the specified condition, the control device can cause the injection instrument to travel back immediately to its original, non-activated position. Alternatively, the control device can discontinue the injection depending on the progress of the injection if the force measurement and/or the capacity measurement indicates a no longer correct positioning of the animal. For example, even with an incorrect positioning of the animal the injection can be continued if almost the whole of the injection preparation has been injected into the animal.

The control device can also continue the injection to the end irrespective of whether the previously occupied correct positioning has been vacated, since the animal by movements temporarily causes a deviating force during the injection. For example, the injection is only discontinued if the deviation of the measured forces and/or the measurement of the capacity sensor deviates from the limit values by a specified amount.

The third force sensor preferably has a bar projecting perpendicular to the pressure application direction, whereby the pressure application area lies against the bar. The bar is preferably made elongated, in particular rectangular. The third force sensor preferably has a base part projecting from the main body in the pressure application direction from which the bar projects sideways. The bar serves in particular for the force transfer of the force acting on the pressure application area to the sensor of the third force sensor. For example, the sensor of the third force sensor is provided on the base part which is arranged offset with respect to the pressure application area. The pressure application area is preferably arranged opposite the injection instrument, so that no space is available on the main body for the attachment of the third force sensor. With the aid of the bar, the offset between base part and pressure application area can be bridged.

The contact area can include at least one opening for the passage of a needle (or optionally several needles) of the injection instrument (or of another discharge-side end of the injection instrument), with the opening preferably being arranged in the pressure application area.

The opening can be configured such that the injection instrument, in particular the needle thereof, can be introduced into the animal through the opening. For example, the opening is made elongated in a horizontal direction, so that even with an arrangement in which the needle is arranged inclined relative to the surface of the main body and/or the contact device, the needle can be passed through the opening.

Since the pressure application area represents a particularly important indicator of the correct positioning of the animal against the contact device, the pressure application area is in particular selected such that it is located at the site of the injection to be carried out, which is represented by the opening. When it is now determined by the third force sensor that the pressing force in the pressure application area is in the specified correct force range, it can be assumed that the injection takes place at the correct site on the animal.

Preferably, two openings are provided in the contact area, wherein each opening is assigned to one needle of the injection instrument. Both the openings are preferably arranged in a horizontal direction, in particular symmetrically to the midline of the contact device. It is however also possible to provide a single opening for both needles.

The injection instrument can be arranged on the main body such that in the non-activated state the needle does not project from the opening. In particular, the injection instrument can be positioned such that after the activation, that is after the operation of the actuator of the injection instrument, its needle protrudes through the opening from the contact area, so that it has been inserted into the animal. Thus the injection takes place through the movement of the needle of the injection instrument and not through a displacement of the contact device. The contact device is preferably mounted movable on the main body in such a manner that when the contact device has been moved completely towards the main body, the needle does not protrude into the opening if the injection instrument is not activated.

Certain embodiments include the advantage that the needle of the injection instrument does not protrude from the contact device, so that there is a low risk of injury (in particular of the persons who push the animals onto the contact area) by the needle of the injection instrument. The injection instrument only moves out from the opening when an animal is correctly positioned, so that there is then also no risk of injury to the user.

The injection device can include a display device on which information concerning the actual positioning of the animal against the contact area based on the measurements of the force measurement device is displayed. The display device can display whether the difference between the force measured by the first force sensor and the second force sensor lies below a specified value and/or whether the force measured by the third sensor lies in the specified range and/or whether the capacitive sensor detects the presence of the animal.

The display device gives the user a visual feedback as to whether the respective measured forces indicate a correct positioning of the animal against the contact device. For example, the user immediately sees whether the force difference lies below the defined limited value, and can thus maintain this positioning and adapt the positioning appropriately with respect to the capacitive sensor and the third force sensor in order also to fulfil the conditions specified there. Thus the correct positioning of the animal against the contact device is facilitated.

The display device preferably displays the difference between the force measured by the first force sensor and the second force sensor and/or the force measured by the third force sensor. For example, the difference between the force measured by the first force sensor and the second force sensor can be displayed by a bar which is elongated in its extent depending on the side of the force excess and its height. Alternatively, the difference can also be represented by a point which, depending on the difference between the force measured by the first force sensor and the second force sensor, moves away from a zero point at which the force measured by the first force sensor and the second force sensor is the same.

The force measured by the third force sensor can be displayed as a bar, wherein a region corresponding to a specified force range is displayed at the same time. Presence in the appropriate force range can for example be additionally emphasized by a changing bar color. The display device accordingly helps the user to implement the correct pressing force and hence the correct positioning of the animal against the contact device.

It is understood that the features named above and those yet to be explained below can be used not only in the stated combinations but also in other combinations or alone, without departing from the scope of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

In the embodiments represented in FIGS. 1 to 6, the injection device 10 comprises a main body 12, a contact device 14, a support device 16, a force measurement device 18, a control device S and a display device 20. The control device S is shown dotted in FIG. 1, since it is positioned within the main body 12.

The injection device 10 serves for administration of injections to an animal. In the embodiment shown, vaccines or medicaments for the treatment of diseases can be administered intramuscularly to a chicken by means of the injection device 10.

Figure 1:
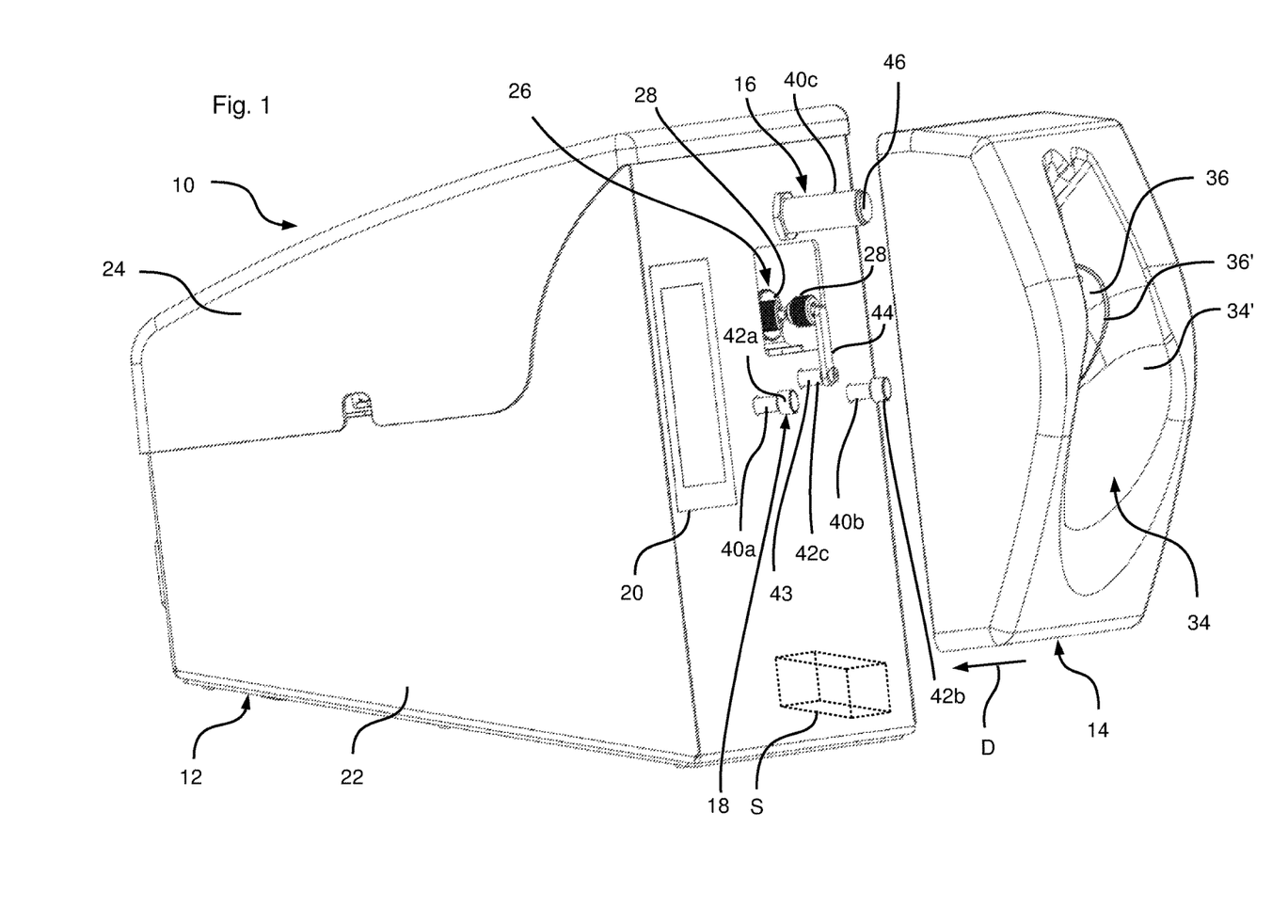
FIG. 1 is a schematic perspective representation of one embodiment of the injection device according to the invention, wherein for better clarity of representation the contact device is shown detached from the main body.

The main body 12 has a housing 22 with a cover 24 attached thereon. The cover 24 can be removed from the housing 22 in order to access an injection instrument 26 arranged in the housing 22.

Figure 2:
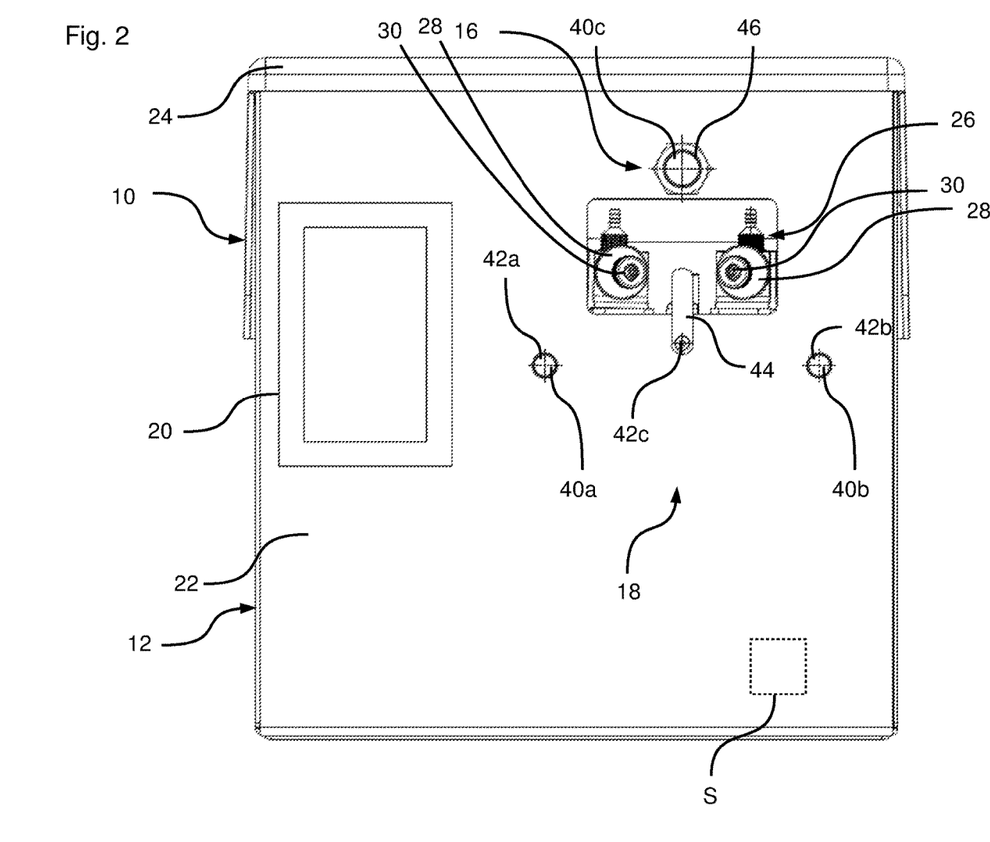
FIG. 2 is a top view of a main body of the injection device according to FIG. 1.
Figure 3:
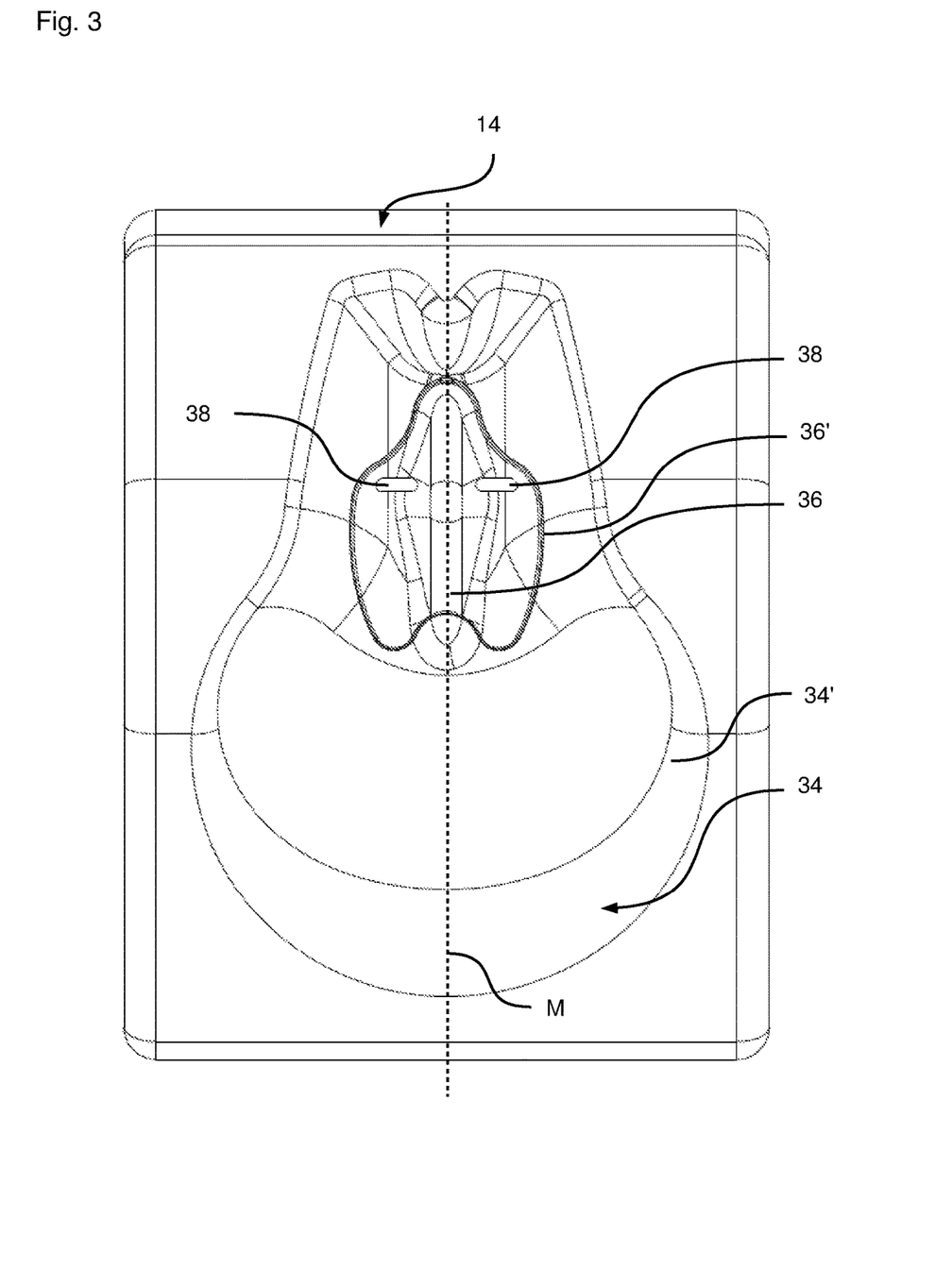
FIG. 3 is a top view of the front side of the contact device of the injection device according to FIG. 1.
Figure 4:
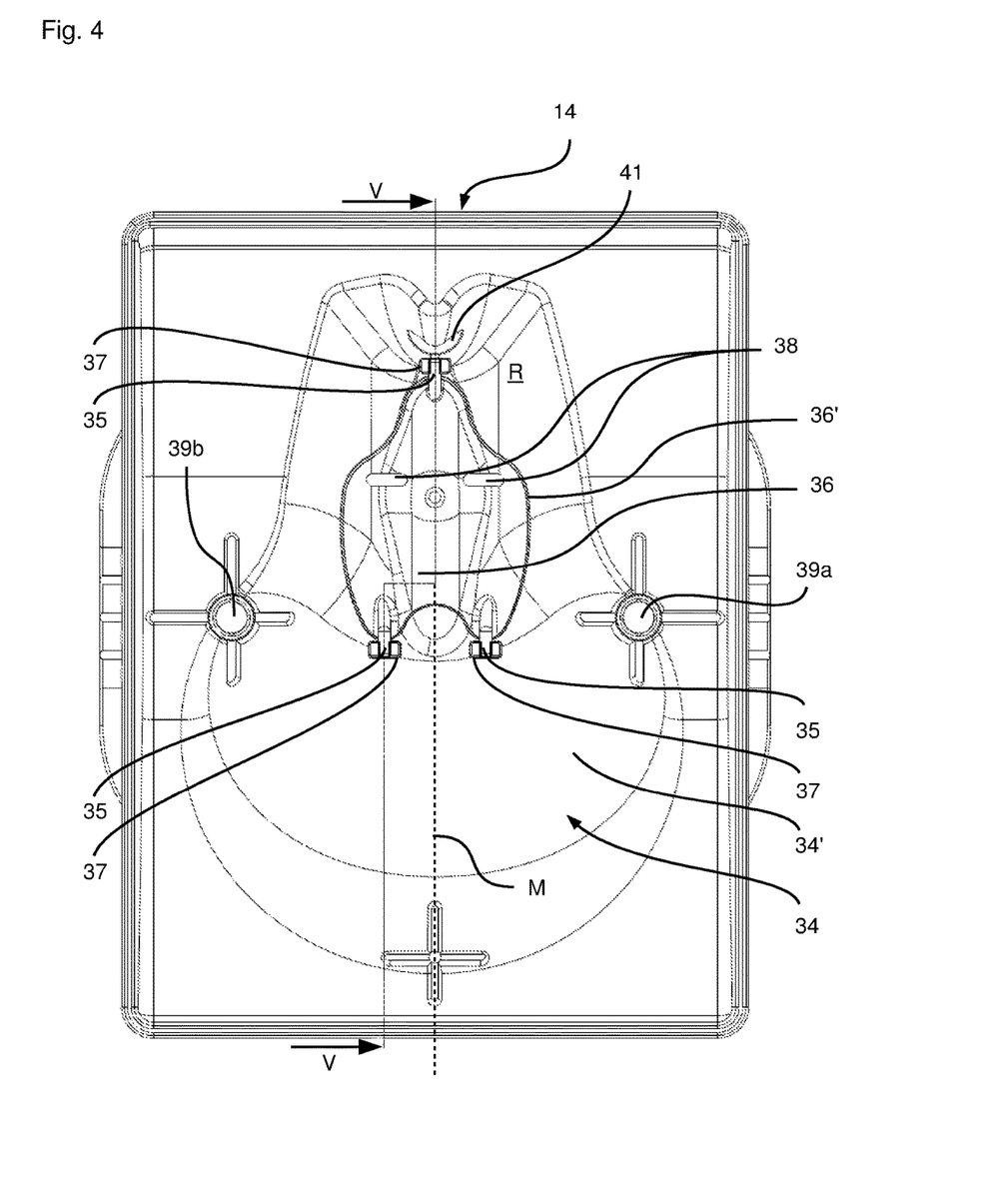
FIG. 4 is a top view of the rear side of the contact device of the injection device according to FIG. 1.
Figure 5:
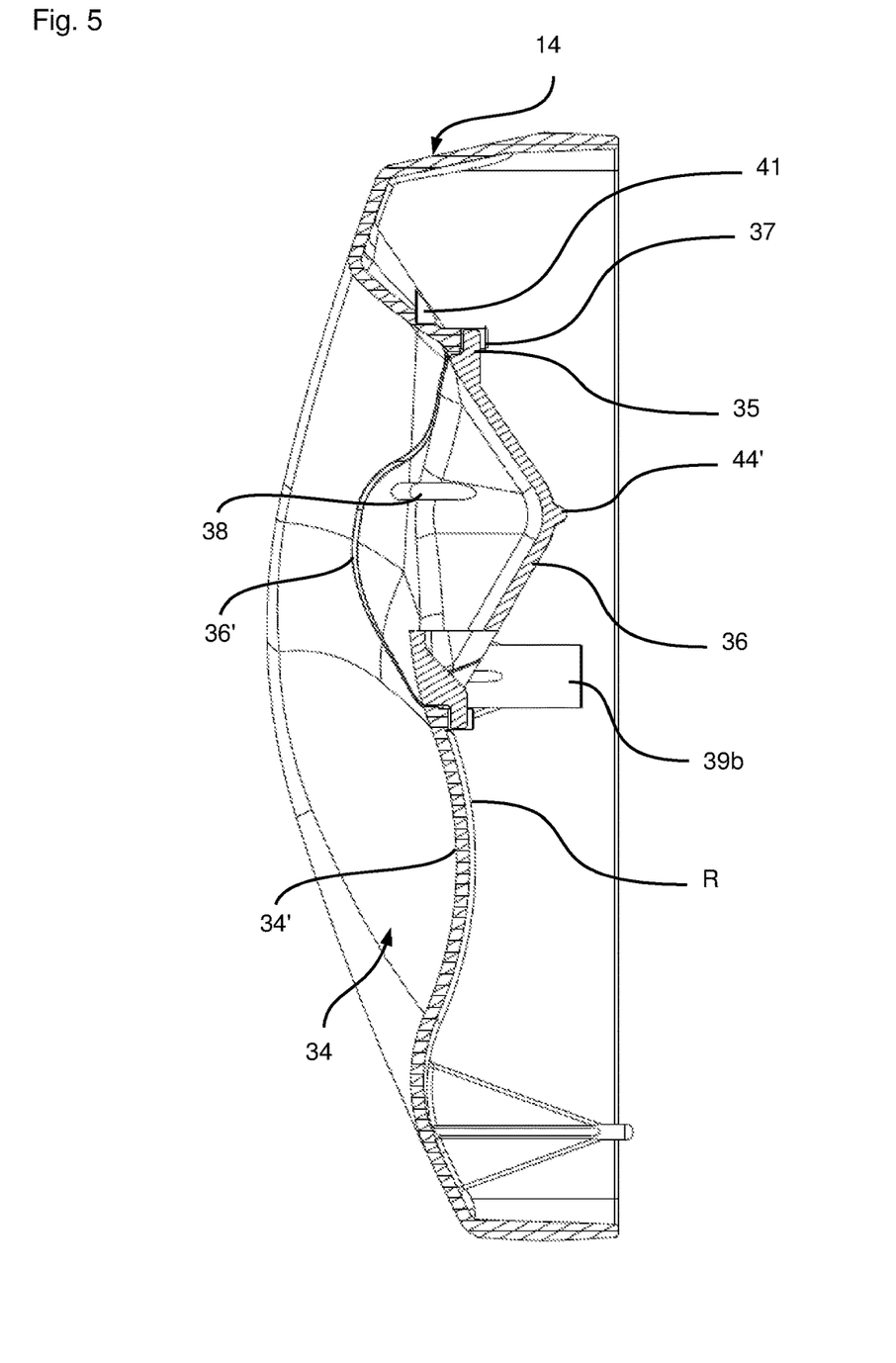
FIG. 5 is an enlarged cross-section view of the contact device of the injection device according to FIG. 1 along the cut line V-V drawn onto FIG. 4.

As can be seen particularly clearly in FIG. 2, the injection instrument 26 comprises two syringes 28 (e.g. self-filling syringes), which each have a needle 30 and an actuator. The actuator moves the needle 30 out from the housing 22 of the main body 12 when the control device S activates the injection instrument 26. In addition, the injection instrument 26 can have a pump or refilling device, not shown, with which injection preparation can be pumped through the needle 30 or which after each injection fills the syringe 28 with the injection preparation for the next injection.

The contact device 14 is arranged movable relative to main body 12 on the basis of the support device 16. In particular, the contact device 14 is assembled removable from the main body 12. Thus different contact devices 14 can be successively attached to the main body 12, with the different contact devices 14 being matched for example to the animal species or breed to be treated, the age of the animals and/or their size.

The contact device 14 has a shaped contact area 34, which is shaped in conformity with the animal and in particular in conformity with the anatomy in the region of the desired injection site. In the embodiment described here, the contact area 34 is shaped in conformity with the breast region of a chicken. The contact area 34 is made in two parts and comprises an outer contact section 34' and an inner pressure application area 36. The outer contact section 34' has a recess 36', in which the pressure application area 36 is positioned such that the outer contact section 34' together with the inner pressure application area 36 form an essentially continuous contact surface for the chicken to be inoculated (apart from a small gap between the outer contact section 34' and the inner pressure application area 36). The pressure application area 36 is shaped in conformity with the size of a breastbone of the chicken and thereby helps to determine the correct positioning of the breastbone of the chicken against the contact device 14, as is further described below. In the pressure application area 36, two openings 38 are provided, as for example is clear from FIG. 3. The openings 38 are positioned corresponding to the syringes 28 of the injection instrument 26 in a horizontal direction symmetrically to a midline M of the contact device 14. After their activation by the control device S, the needles 30 of the syringes 28 move into the breast muscle of the chicken through the openings 38.

The pressure application area 36 is arranged movable relative to the contact section 34' in a pressure application direction D (FIG. 1). For this, the pressure application area 36 has three separate projections 35, which project on the rear side R of the contact section 34' over the recess 36' and are guided in three slots 37, which are made on the rear side R. The slots 37 are made such that the pressure application area 36 is held and that a movement of the projections 35 and thus of the pressure application area 36 in the pressure application direction D is possible. The possible travel is 2 mm.

The support device 16 has three pillar-shaped support elements 40a, 40b, 40c. As can be seen clearly in FIG. 2, the support elements 40a-40c have a cylindrical shape, so that the contact device 14 can be pushed onto the support elements 40a-40c. For this, the contact device 14 has two cylindrical cavities 39a and 39b, shown in FIG. 4, which are matched to the size of the support elements 40a and 40b. The length of the support elements 40a and 40b and the depth of the cavities 39a and 39b in the contact device 14 are selected such that at the maximum push-in depth of the contact device 14 this is at a distance from the main body 12. The contact device 14 is lies against the third support element 40c by means of a contact surface 41.

In the representation of FIG. 1, for better clarity the contact device 14 is shown, in the form of an exploded view, at a distance from the main body 12. Naturally, during the operation of the injection device 10 the contact device 14 sits on the support elements 40a, 40b and 40c and is guided by these such that the contact device 14 is movable along the pressure application direction D.

The first support element 40a is positioned at a distance from the second support element 40b in a horizontal direction, in particular symmetrically to the injection instrument 26. On the axis of symmetry of the first support element 40a and the second support element 40b, the third support 40c is arranged offset in a vertical direction which is perpendicular to the horizontal direction. The axis of symmetry coincides with a midline M of the contact device 14.

The force measurement device 18 comprises three force sensors 42a, 42b and 42c, which are each designed as a weighing cell known from the prior art. A first force sensor 42a is built into the first support element 40a, while a second force sensor 42b is positioned in the second support element 40b.

A third force sensor 42c is positioned on the midline M. The third force sensor 42c has a base part 43 and a bridge or bar 44. The bridge 44 extends up to the openings 38, while its free end lies somewhat below the openings 38. The bridge 44 is provided since, because of the anatomy of the chicken and in particular the breastbone, for which the pressure application area 36 is provided, the section projecting the furthest in the direction of the main body 12 lies in the region of the two openings 38. In this region, because of the two syringes 28, there is not sufficient space in the main body 12 for the third force sensor 42c. The bridge 44 is therefore provided for force transfer from the pressure application area 36 to the third force sensor 42c. As can be seen from FIG. 5, the pressure application area 36 has a projecting contact section 44', which during the operation of the injection device presses against the bridge 44 at the free end of the bridge 44.

The injection device 10 further has a capacitive sensor 46, which is positioned at the end of the third support element 40c facing the contact device 14. The capacitive sensor 46 detects the presence of an animal in its vicinity. For this, in the region adjacent to the capacitive sensor 46 the contact device 14 is designed in such a manner that it does not interfere with the capacity measurement of the capacitive sensor 46. By means of the capacitive sensor 46, it can be determined whether the animal is positioned in an upper peripheral region of the contact area 34.

Figure 6:
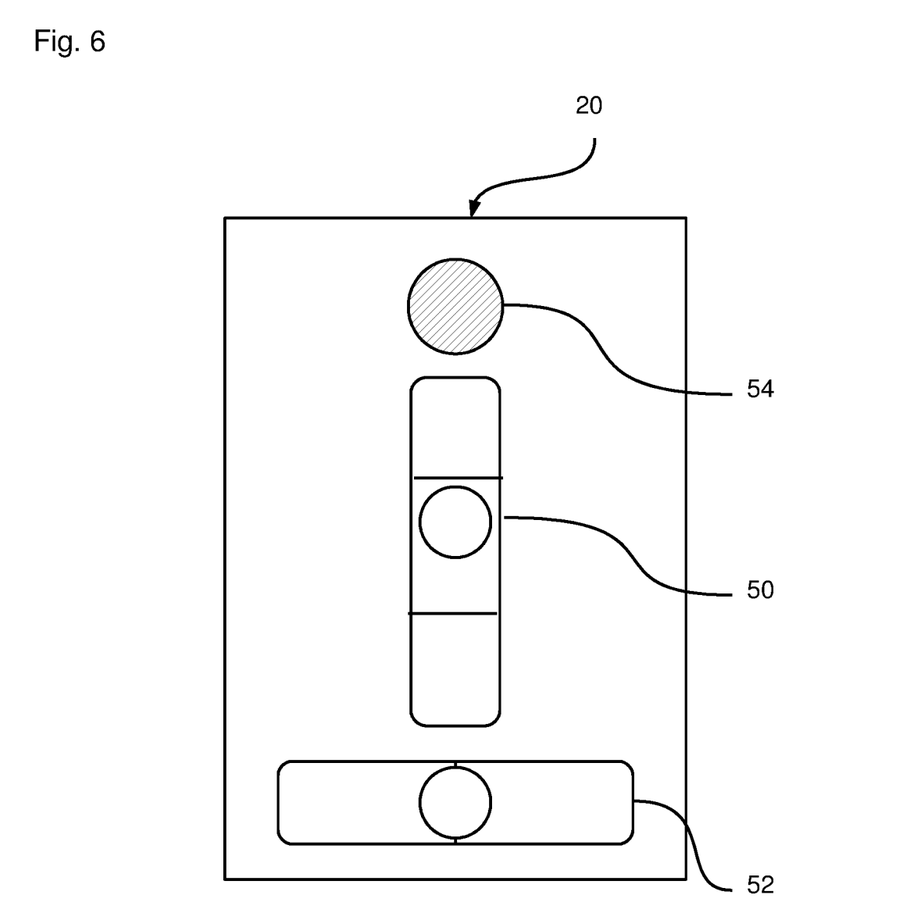
FIG. 6 is a top view of a display device of the injection device according to FIG. 1.

As can be seen in FIG. 6, the display device 20 shown enlarged in FIG. 6 has a display 50 for the force measured by means of the third force sensor 42c, a display 52 for the difference of the force measured by means of the first force sensor 42a and the second force sensor 42b and a display 54 for the capacitive sensor 46.

The display 50 shows the force measured by means of the force sensor 42c in the form of a point the vertical positioning whereof indicates the magnitude of the force. The display 50 further has markings which correspond to the specified force range. In the embodiment shown, the point is located in the specified force range, so that the force applied to the pressure application area 36 lies in the specified range.

In the case of the display 52, it is shown by means of the position of a point whether the force applied to the first force sensor 42a or to the second force sensor 42b is greater than the force applied to the respective other force sensors. In the embodiment shown, the point is located in the middle of the display 52, which indicates that the force applied to the first force sensor 42a or to the second force sensor 42b is of equal magnitude. The display 54 is designed as a lamp, wherein the illumination of the display 54 indicates that the capacitive sensor 56 has detected the presence of the animal.

The mode of functioning of the injection device 10 is explained below:

A user of the injection device 10 holds an animal against the contact device 14. By correct positioning of the animal against the contact area 34, that is by application of the appropriate pressing force, the control device S triggers an injection. For this, the force difference between the force measured by the first force sensor 42a and the second force sensor 42b must lie below a certain limit value, that is, the force balance in the horizontal direction must be present. This indicates that the animal is not being pushed on obliquely. If the force balance is present and a force in the specified range is present on the third force sensor 42c, the control device S activates the injection instrument 26 and the injection is performed, if further the presence of the animal is detected by means of the capacitive sensor 46.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. Injection device for administration of an injection to an animal, comprising:
    an injection instrument;
    a main body which contains said injection instrument;
    a contact device which has a contact area which is shaped in conformity with a body part of the animal to which the injection is to be administered;
    a support device which supports the contact device on the main body movable in a pressure application direction;
    a force measurement device including at least one force sensor, which is configured to measure at least one force with which the contact device acts on the main body; and
    a control device which is configured to activate the injection instrument if the at least one force measured by the force measurement device lies in a specified range,
    wherein the contact area comprises a contact section and a pressure application area, each movable in the pressure application direction, and
    wherein the pressure application area is movable independent of movement of the contact section.

2. The injection device according to claim 1, wherein the force measurement device comprises a first force sensor and a second force sensor at a distance therefrom, wherein the control device can only activate the injection instrument if the difference between the force measured by the first force sensor and the second force sensor lies below a specified value.

3. The injection device according to claim 2, wherein the pressure application area is movable relative to the contact section.

4. The injection device according to claim 3, wherein the pressure application area is disposed in a recess of the contact section.

5. The injection device according to claim 4, wherein the force measurement device includes a third force sensor positioned on the main body, wherein the third force sensor is designed to measure the force acting on the pressure application area, and wherein the control device is configured to only activate the injection instrument if the force measured by the third force sensor lies in a specified range.

6. The injection device according to claim 3, wherein the force measurement device includes a third force sensor positioned on the main body, wherein the third force sensor is designed to measure the force acting on the pressure application area, and wherein the control device is configured to only activate the injection instrument if the force measured by the third force sensor lies in a specified range.

7. The injection device according to claim 3, wherein the first and second force sensors are configured to measure forces to which they are subjected by the contact section.

8. The injection device according to claim 1, wherein the injection device includes a capacitive sensor configured to detect the presence of the animal against the contact area, and wherein the control device is configured to can only activate the injection instrument if the capacitive sensor detects the presence of the animal.

9. The injection device according to claim 8, wherein the contact area comprises a contact section and a pressure application area which is movable in the pressure application direction relative to the contact section.

10. The injection device according to claim 9, wherein the pressure application area is disposed in a recess of the contact section.

11. The injection device according to claim 10, wherein the force measurement device includes a third force sensor positioned on the main body, wherein the third force sensor is designed to measure the force acting on the pressure application area, and wherein the control device is configured to only activate the injection instrument if the force measured by the third force sensor lies in a specified range.

12. The injection device according to claim 9, wherein the force measurement device includes a third force sensor positioned on the main body, wherein the third force sensor is designed to measure the force acting on the pressure application area, and wherein the control device is configured to only activate the injection instrument if the force measured by the third force sensor lies in a specified range.

13. The injection device according to claim 1, wherein the pressure application area is movable relative to the contact section.

14. The injection device according to claim 13, wherein the pressure application area is disposed in a recess of the contact section.

15. The injection device according to claim 14, wherein the force measurement device includes a third force sensor positioned on the main body, wherein the third force sensor is designed to measure the force acting on the pressure application area, and wherein the control device is configured to only activate the injection instrument if the force measured by the third force sensor lies in a specified range.

16. The injection device according to claim 13, wherein the force measurement device includes a third force sensor positioned on the main body, wherein the third force sensor is designed to measure the force acting on the pressure application area, and wherein the control device is configured to only activate the injection instrument if the force measured by the third force sensor lies in a specified range.

17. The injection device according to claim 1, wherein the contact area includes at least one opening for passage of a needle of the injection instrument.

18. The injection device according to claim 17, wherein the injection instrument is positioned on the main body in such a manner that in the non-activated state of the injection instrument the needle does not protrude from the opening.

19. The injection device according to claim 1, wherein the injection device includes a display device on which information relating to the actual positioning of the animal against the contact area can be displayed on the basis of the measurements of the force measurement device.

20. Injection device for administration of an injection to an animal, comprising:
    an injection instrument;
    a main body which contains said injection instrument;

a contact device which has a contact area which is shaped in conformity with a body part of the animal to which the injection is to be administered;

a support device which supports the contact device on the main body movable in a pressure application direction;

a force measurement device including at least one force sensor, which is configured to measure at least one force with which the contact device acts on the main body; and a control device which is configured to activate the injection instrument if the at least one force measured by the force measurement device lies in a specified range, wherein the contact area comprises a contact section and a pressure application area, each movable in the pressure application direction, and wherein the pressure application area is movable in the pressure application direction relative to the contact section.

* * * * *